United States Patent [19]

Kaufhold

[11] Patent Number: 5,728,836
[45] Date of Patent: Mar. 17, 1998

[54] PROCESS FOR PREPARING 4-ACYLAMINO-2,2,6,6-TETRAMETHYLPIPERIDINES

[75] Inventor: Manfred Kaufhold, Marl, Germany

[73] Assignee: Huels Aktiengesellschaft, Marl, Germany

[21] Appl. No.: 704,863

[22] Filed: Aug. 30, 1996

[30] Foreign Application Priority Data

Sep. 1, 1995 [DE] Germany .................. 195 32 215.0

[51] Int. Cl.$^6$ .................................................. C07D 211/98
[52] U.S. Cl. ............................................................. 546/244
[58] Field of Search ............................................. 546/244

[56] References Cited

U.S. PATENT DOCUMENTS 5,416,215  5/1995  Büschken et al. .

FOREIGN PATENT DOCUMENTS 0 387 489   9/1990   European Pat. Off. .
38 00 987   7/1989   Germany .

OTHER PUBLICATIONS

Journal of Organic Chemistry, vol. 56, No. 21, pp. 6110–6114, Oct. 11, 1991, Zhenkun MA, et al., "Organic Oxoammonium Salts—A New Convenient Method for the Oxidation of Alcohols to Aldehydes and Ketones".

Chemical Abstracts, vol. 66, No. 13, AN–54758, Mar. 27, 1967.

Primary Examiner—C. Warren Ivy
Assistant Examiner—Raymond Covington
Attorney, Agent, or Firm—Oblon, Spivak, McClelland, Maier & Neustadt, P.C.

[57] ABSTRACT

Preparation of 4-acylamino-2,2,6,6-tetramethylpiperidines from 4-amino-2,2,6,6-tetramethylpiperidine and acid anhydrides carried out in the presence of carboxylic acids, whereupon the carboxylic acid is eliminated, using water at elevated temperature, from the initially formed carboxylate salt of the 4-acylamino-2,2,6,6-tetramethylpiperidine. In this process, no salt-like by-products arise.

13 Claims, No Drawings

PROCESS FOR PREPARING 4-ACYLAMINO-2,2,6,6-TETRAMETHYLPIPERIDINES

BACKGROUND OF THE INVENTION

1. Field of the Invention

The invention relates to a novel process for the preparation of 4-acylamino-2,2,6,6-tetramethylpiperidines from 4-amino-2,2,6,6-tetramethylpiperidine and acid anhydrides.

2. Discussion of the Background

4-Acylamino-2,2,6,6-tetramethylpiperidines are used as fungicides. They are, moreover, important intermediates for the preparation of the corresponding n-oxyls, which are used as stabilizers for olefinically unsaturated compounds, such as styrene or acrylic acid.

The preparation of amides of 4-amino-2,2,6,6-tetramethylpiperidine, which is also called triacetonediamine (TAD), is disclosed in the literature. Thus Harries, in Annalen, volume 417 (1918) describes on page 120 the preparation of the acetate salt of acetaminotetramethylpiperidine by "treating aminopiperidine with acetic anhydride". In a second stage, the acetate salt is dissolved in water and neutralized with sodium hydroxide solution, the acetaminotetramethylpiperidine precipitating out in crystalline form. In this two-stage process, large equimolar amounts of sodium acetate are produced, which must be disposed of in the case of industrial production.

In EP-A-0 387 489, it is proposed to react TAD with an acid chloride. In this process, common salt, whose disposal is technically complex and thus costly, is produced in equimolar amounts. When acid chlorides are employed, a salt-like obligatory product is unavoidable.

SUMMARY OF THE INVENTION

It is the object of the present invention to provide a process for the preparation of 4-acylamino-2,2,6,6-tetramethylpiperidines from TAD and acid anhydrides in which no salt-like wastes arise. The object is surprisingly achieved by carrying out the reaction in the presence of carboxylic acids and eliminating the carboxylic acid, using water at elevated temperature, from the initially prepared carboxylate salt of the 4-acylamino-2,2,6,6-tetramethylpiperidine.

DESCRIPTION OF THE PREFERRED EMBODIMENTS

The reaction can be described by the following reaction scheme:

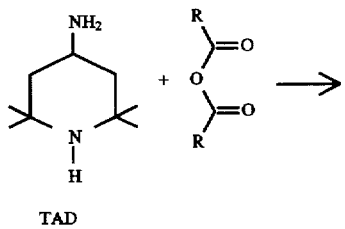

TAD

-continued

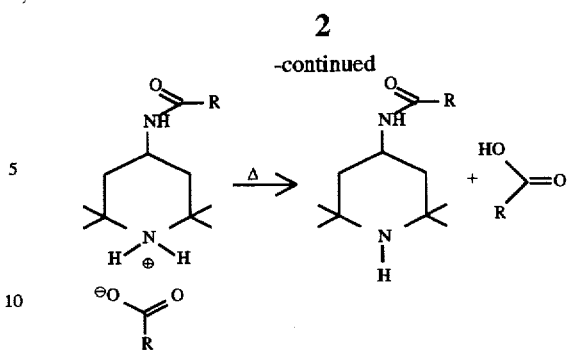

The substituents R are in this case preferably alkyl having 1 to 7 carbon atoms or phenyl.

Examples of alkyl substituents are methyl, ethyl, n-propyl, iso-propyl, n-butyl, iso-butyl, pentyl, hexyl or iso-heptyl. In general, the two substituents R in the anhydride are identical, although mixed anhydrides can also be used. Preferably, the added carboxylic acid also has the same radical R as the acid anhydride.

Particularly preferably, R is an alkyl radical having 1 to 3 carbon atoms.

The reaction is preferably carried out at 80° to 160° C. and the cleavage is performed with addition of water at 150° to 250° C., preferably 170° to 250° C. Most preferably, a reaction temperature of 90° to 120° C. is set and the acid is eliminated and distilled off at 190° to 210° C.

It is surprising that cleavage of the initially arising salt-like compound can be carried out with success using water even at approximately 150° C. The thermal cleavage process of the invention by addition of water is a particularly gentle method. In this method, a mixture of water and carboxylic acid is distilled off. The end of the salt cleavage process is achieved when the distillate no longer contains acid.

In some cases, elimination of the carboxylic acid bound as a salt is associated with intense sublimation. In these cases, an additional solvent which boils higher than the acid to be eliminated is advantageous. Thus an additional solvent of this type suppresses, for example, sublimation during the elimination of acetic acid accelerated by water in the preparation of acetyl-TAD. The temperature is set in this case in such a way that the solvent in the reaction bottom boils and is condensed again on the upper, colder sites of the reactor. This prevents solidification of sublimate, while at the same time a mixture of acetic acid and water distills off over a column. When acetic acid no longer distills with the water, the solvent can also be distilled off. However, the product can also be recrystallized in the solvent.

Suitable solvents preferably have a boiling point in the range from 150° to 270° C. Those which can be used are, for example, hydrocarbons, alcohols, esters, ethers and chlorinated hydrocarbons. For economic reasons customarily inexpensive products, such as oxo-alcohols, are used. 2-Ethylhexanol and its acetate are also suitable, for example. The solvent can be added during the elimination of carboxylic acid or at an earlier time.

For the reaction with TAD, carboxylic acid and carboxylic anhydride are preferably used in a weight ratio of 10:1 to 1:10. Particularly preferably, a weight ratio of 5:1 to 1:2 is set.

Preferably, carboxylic anhydride and TAD are employed in a molar ratio of 4:1 to 1:1. Molar ratios of 1.5:1 to 1.1:1 are particularly preferred.

The amount of water depends on the size of the apparatus and the distillation conditions employed. Water or steam is added into the reaction mixture until the aqueous condensate arising contains no carboxylic acid, or only small amounts.

The function of the solvent is to dissolve sublimate arising in the upper part of the reactor and to wash it into the bottom. The solvent/TAD weight ratio is generally 5:1 to 1:10 and in particular cases 1:1 to 1:3.

A particular advantage of the process of the invention is that only readily disposable liquid by-products are produced, which, for the most part, as with the acid solvent, can be recovered and reused.

Further advantages are the gentle conditions of the process and that acetyl-TAD, for example, is obtained in very high yields (above 90%) and isomerically pure.

The nitrogen in the six-membered ring, under the conditions employed, does not react with acetic anhydride to form a covalent bond. This is surprising, since in DE-A38 00 987, a process is described for the preparation of N-acetyl-2,2, 6,6-tetramethyl-4-piperidine, in which the so-called triacetoneamine is reacted with acetic anhydride, the nitrogen in the six-membered ring therefore being reacted.

When the process of the present invention is carried out, a stirred apparatus having an attached distillation column is used, for example. A mixture of carboxylic acid and carboxylic anhydride is introduced and heated to the desired reaction temperature, whereupon TAD is then added. After the reaction, excess acid anhydride and free carboxylic acid are distilled off, a liquid, readily stirrable melt of the intermediate remaining in the flask.

Water or steam and, if appropriate, a solvent are then added, an aqueous acid being distilled. When the acid is completely or substantially distilled off, the desired product is present as melt or dissolved in the added solvent. In the first case, the product can be distilled directly. In the second case, it can be concentrated, whereupon the product may be crystallized out. However, the solvent can alternatively be distilled first and then the product.

German patent application 195 32 215.0 filed Sep. 1, 1995 is incorporated herein by reference, in its entirety.

The following examples are intended to clarify the invention without limiting it.

EXAMPLE 1

A glass set-up comprising a four-neck flask having a dropping funnel, stirrer, thermometer, distillation column and distillation bridge with receiver are used.

The following are introduced into the flask:

225 g (2.14 mol) of acetic anhydride (97% pure)

400 g of acetic acid (99.8% pure)

The mixture is then heated to 90° C. and, in the course of 2 hours, 313 g (2.0 mol) of TAD (99.8% pure) are added at this temperature. The mixture is then heated to 100° C. and further stirred for one hour.

To determine the conversion rate, a sample is diluted with methanol, neutralized with sodium hydroxide solution and analyzed by gas chromatography. The content of TAD is less than 0.1%, i.e. TAD is virtually completely converted. The temperature is then increased from 100° to 200° C. As distillate, 368 g of pure acetic acid are obtained, then 150 g of 2-ethylhexanol are added rapidly at a constant temperature of 200° C.

The addition of water is then begun at a rate of 60 ml/h. The distillate flow rate is initially considerably greater than that of the water used, in the course of 2 hours it decreases from 65 ml per half hour to 35 ml per half hour. After 3 hours, the acid number of a distillate sample, which is two-phase, is below 3.0. The elimination of the acetic acid is thus ended.

At a constant bottom temperature of 200° C., 2-ethylhexanol is then distilled off by decreasing the pressure to initially 400 and, in the course of 3 hours, to 30 mbar. 127 Grams of distillate are obtained, which comprises 38% of 2-ethylhexanol and 60% of its acetate.

The bottom product is a pure, brown acetyl-TAD, whose contents of TAD, 2-ethylhexanol and acetate of the 2-ethylhexanol are below 0.1%. 364.5 g are obtained. This corresponds to a yield of approximately 92%, based on the TAD used.

This product is suitable as starting material for the preparation of the N-oxyl. For this purpose, it is suspended in water, admixed with catalyst and oxidized with hydrogen peroxide. After reaction is completed, the solution is cooled and the N-oxyl of the acetyl-TAD is obtained by filtration.

EXAMPLE 2

The set-up described in Example 1 is used and the following are added:

355 g (2.2 mol) of butyric anhydride (98% pure)

180 g of butyric acid

The mixture is heated to 80° C., whereupon 313 g (2.0 mol) of TAD (98% pure) are added in the course of 4 hours at this temperature. The mixture is then heated in the course of 1 hour to 120° C. and stirred at this temperature for 1 hour. The conversion of TAD is then complete. The butyric acid is distilled off by heating to 220° C.

Tetralin is then added as solvent at 220° C. and butyric acid is then eliminated by addition of water—as described in Example 1. The added tetralin is then distilled off in vacuo.

The desired amide of butyric acid and TAD is obtained in a purity of 98% and a yield, based on TAD used, of 94%.

Obviously, numerous modifications and variations of the present invention are possible in light of the above teachings. It is therefore to be understood that within the scope of the appended claims, the invention may be practiced otherwise than as specifically described herein.

We claim:

1. A process for preparing a 4-acylamino-2,2,6,6-tetramethylpiperidine comprising:

contacting 4-amino-2,2,6,6-tetramethylpiperidine and an acid anhydride in the presence of added carboxylic acid thereby forming a carboxylate salt of the 4-acylamino-2,2,6,6-tetramethylpiperidine, and eliminating said carboxylic acid from the reaction mixture using water at elevated temperature.

2. The process as claimed in claim 1, wherein said acid anhydride has the structure

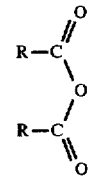

where R is alkyl having 1 to 7 carbon atoms or phenyl.

3. The process as claimed in claim 1, wherein the reaction is carried out at 80° to 160° C. and the elimination is carried out at 170° to 250° C.

4. The process as claimed in claim 3, wherein the reaction is carried out at 90° to 120° C. and the elimination is carried out at 190° to 210° C.

5. The process as claimed in claim 1, wherein the carboxylic acid is eliminated in the presence of a solvent having a boiling point from 150° to 270° C.

6. The process as claimed in claim 1, wherein carboxylic acid and carboxylic anhydride are used in a weight ratio of 10:1 to 1:10.

7. The process as claimed in claim 1, wherein carboxylic anhydride and 4-amino-2,2,6,6-tetramethylpiperidine are used in a molar ratio of 4:1 to 1:1.

8. A process for preparing a 4-acylamino-2,2,6,6-tetramethylpiperidine comprising:

contacting a mixture of an acid anhydride and a carboxylic acid with 4-amino-2,2,2,6,6-tetramethylpiperidine to form a carboxylate salt of the 4-acylamino-2,2,6,6-tetramethylpiperidine, and eliminating said carboxylic acid from the reaction mixture using water at elevated temperature, said acid anhydride having the structure

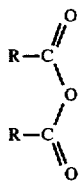

wherein R is alkyl having 1 to 7 carbon atoms or phenyl, and, said carboxylic acid having the structure and

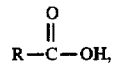

wherein R is alkyl having 1 to 7 carbon atoms or phenyl.

9. The process of claim 8 wherein said carboxylic acid also has the same radical R as the acid anhydride.

10. The process of claim 1, wherein R is an alkyl radical having 1 to 3 carbon atoms.

11. The process of claim 8, wherein said acid anhydride is acetic anhydride and said carboxylic acid is acetic acid.

12. The process of claim 8, wherein said acid anhydride is butyric anhydride and said carboxylic acid is butyric acid.

13. The process of claim 11, wherein the nitrogen in the sixth member ring of the piperidine structure does not react with acetic anhydride to form a covalent bond.

* * * * *